(12) United States Patent
Debrauwer et al.

(10) Patent No.: US 12,202,994 B2
(45) Date of Patent: Jan. 21, 2025

(54) THERMOCHROMIC PIGMENT COMPOSITIONS

(71) Applicant: SOCIETE BIC, Clichy (FR)

(72) Inventors: Christelle Debrauwer, Saint Germain sur Morin (FR); Anne-Lise Damiano, Lagny sur Marne (FR); Alexander Bourque, Montevrain (FR); Francois Foulonneau, Bordeaux (FR); Guillaume Chollet, Leognan (FR)

(73) Assignee: SOCIETE BIC, Clichy (FR)

( * ) Notice: Subject to any disclaimer, the term of this patent is extended or adjusted under 35 U.S.C. 154(b) by 855 days.

(21) Appl. No.: 16/608,321

(22) PCT Filed: Apr. 24, 2018

(86) PCT No.: PCT/FR2018/051033
§ 371 (c)(1),
(2) Date: Mar. 21, 2022

(87) PCT Pub. No.: WO2018/197809
PCT Pub. Date: Nov. 1, 2018

(65) Prior Publication Data
US 2021/0102083 A1     Apr. 8, 2021

(30) Foreign Application Priority Data
Apr. 27, 2017   (FR) ...................... 1753680

(51) Int. Cl.
  *C09D 11/50*   (2014.01)
  *B41M 5/337*   (2006.01)
  (Continued)

(52) U.S. Cl.
  CPC ........... *C09D 11/50* (2013.01); *B41M 5/3375* (2013.01); *C07C 69/612* (2013.01);
  (Continued)

(58) Field of Classification Search
  CPC .. B41M 5/305; B41M 5/3275; B41M 5/3335; B41M 5/3375; C07C 69/612; C07C 69/616; C09D 11/17; C09D 11/50
  See application file for complete search history.

(56) References Cited

U.S. PATENT DOCUMENTS

| 2,503,701 A | 4/1950 | Mortimer |
| 4,720,301 A | 1/1988 | Tsotomu et al. |
| 2005/0090593 A1 | 4/2005 | Heuer et al. |

FOREIGN PATENT DOCUMENTS

| EP | 3009493 | 4/2016 | |
| JP | 61149393 A | * 7/1986 | .......... B41M 5/3375 |

(Continued)

OTHER PUBLICATIONS

International Search Report dated Aug. 23, 2018 for PCT application No. PCT/FR2018/051033.

(Continued)

*Primary Examiner* — Gerard Higgins
(74) *Attorney, Agent, or Firm* — Ruggiero McAllister & McMahon LLC

(57) ABSTRACT

A thermochromic pigment composition including: (A) at least one electron-donor organic dye compound, (B) at least one electron-acceptor compound, and (C) at least one compound responding to the following formula (I), in which: $R_1$ is H or a phenyl group, $-R_2$ is H or a phenyl group, and -n=1-8. The thermochromic pigment composition includes thermochromic pigment microcapsules ink compositions including such thermochromic pigment microcapsules, and writing instruments including such ink compositions.

9 Claims, 1 Drawing Sheet

(51) Int. Cl.
*C07C 69/612* (2006.01)
*C07C 69/616* (2006.01)
*C09D 11/17* (2014.01)
*B41M 5/30* (2006.01)
*B41M 5/327* (2006.01)
*B41M 5/333* (2006.01)

(52) U.S. Cl.
CPC ............ *C07C 69/616* (2013.01); *C09D 11/17* (2013.01); *B41M 5/305* (2013.01); *B41M 5/3275* (2013.01); *B41M 5/3335* (2013.01)

(56) References Cited

FOREIGN PATENT DOCUMENTS

| WO | 2016198784 A1 | 12/2016 | |
|---|---|---|---|
| WO | WO-2017101115 A1 * | 6/2017 | ................ D06P 1/60 |

OTHER PUBLICATIONS

International Search Report dated Aug. 16, 2018 in related PCT application No. PCT/FR2018/051032, 2 pages.
International Search Report dated Aug. 10, 2018 in related PCT application No. PCT/FR2018/051031, 2 pages.
Amorati et al, "Synthesis of new Cardonal and Cardo derivatives by allylation and regioselctive cyclocarbonylation reactions", Synthesis, No. 18, Jan. 1, 2002, Georg Thieme Verlag, Stuttgart, DE, pp. 2749-2755.
Kaufmann et al, "To know the Cashew-ole II about some derivatives of the main components of the shell folk". Jan. 1, 1967 (Jan. 1, 1967). pp. 577-579.

* cited by examiner

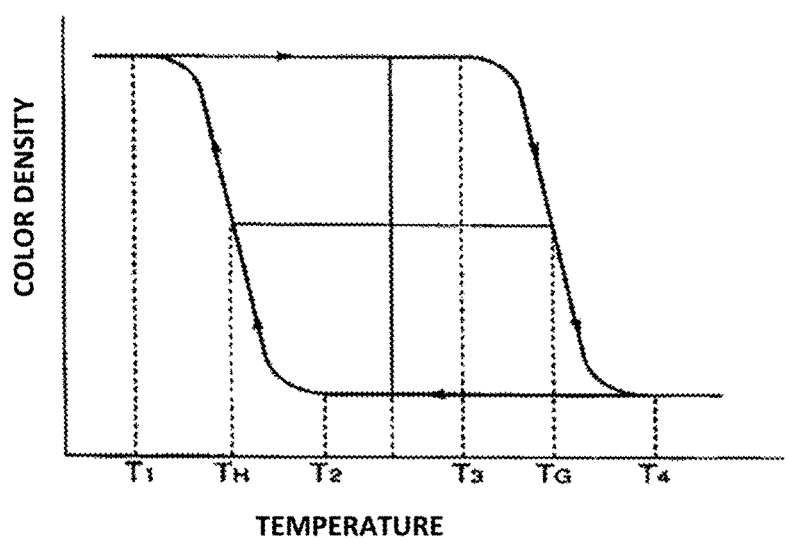

THERMOCHROMIC PIGMENT COMPOSITIONS

CROSS REFERENCE TO RELATED APPLICATIONS

This application is a National Stage application of International Application No. PCT/FR2018/051033, filed on Apr. 24, 2018, now published as WO/2018/197809 and which claims priority to French Application No. 1753680, filed Apr. 27, 2017, the entire contents of which is incorporated herein by reference.

FIELD

The present disclosure relates to thermochromic pigment compositions comprising specific compounds as reaction medium. The present disclosure also relates to thermochromic pigment microcapsules comprising such thermochromic pigment compositions, to ink compositions comprising such thermochromic pigment microcapsules, and finally to writing instruments comprising such ink compositions.

DESCRIPTION OF RELATED ART

Thermochromic pigment compositions present reversible decoloration properties relating to a temperature change. These compositions are used when an ink marking requires repeated erasure.

The thermochromic effect of an ink works thanks to the association of the three following compounds:
(A) at least one electron-donor organic dye or leuco dye compound,
(B) at least one electron-acceptor or color developer compound, and
(C) at least one compound serving as a reaction medium, capable of bringing about a reversible electron-acceptance/donation reaction that can be attributed to compounds (A) and (B) or a temperature change regulation agent.

Temperature changes reversibly cause the coloration or decoloration of inks. Thus, an increase in temperature will cause the erasure of the ink, while cooling will cause its appearance. These changes follow the graph in FIG. 1. In FIG. 1, the initial color disappearance temperature of the ink is T3, that at which the color of the ink has totally disappeared is T4, and TG is the medium temperature between T3 and T4. Conversely, the initial color reappearance temperature of the ink is T1, and TH is the temperature between T1 and T2. The range between (TH) and (TG) is called the color change hysteresis range ($\Delta H$).

SUMMARY

The present disclosure relates to thermochromic pigment compositions where specific compounds are able to be used as a reaction medium in thermochromic pigment compositions. The compositions allow the preparation of thermochromic pigment microcapsules presenting optimal fusion and crystallization temperature ranges corresponding to the decoloration and recoloration temperatures of these compounds, respectively. The compounds of the present disclosure thus present numerous advantages to be used as a temperature change regulating agent in thermochromic inks: it has remarkable hysteresis characteristics and an extremely high color contrast between the colored state and the decolored state.

DETAILED DESCRIPTION

According to a first embodiment, the technical objective is to provide a thermochromic pigment composition comprising:
(A) at least one electron-donor organic dye compound,
(B) at least one electron-acceptor compound, and
(C) at least one compound responding to the following formula (I):

(I)

wherein:
$R_1$ represents H or a phenyl group,
$R_2$ represents H or a phenyl group, and
n=1-8.

In the formula (I) above, n may be independently chosen from among the following integers: 1, 2, 3, 4, 5, 6, 7 or 8.

Advantageously, in the formula (I) above, $R_1$ and $R_2$ are identical.

According to a first embodiment the compound (C) responds to the following formula ($I_a$):

($I_a$)

wherein n=1-8.

According to a second embodiment, the compound (C) responds to the following formula ($I_b$):

($I_b$)

wherein n=1-8.

The compounds of formula (I) can be synthesized using two different synthesis routes.

The first synthesis route responds to the following reaction (when $R_1=R_2$):

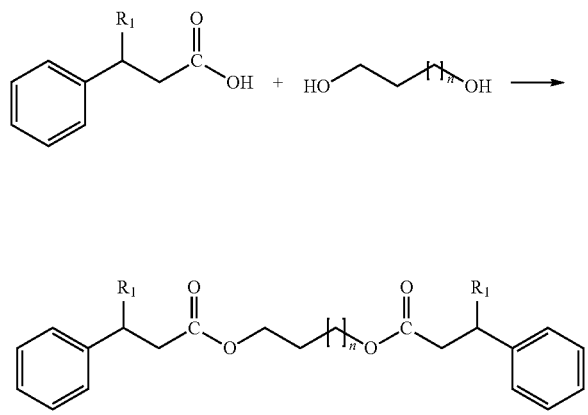

In this first synthesis route the alcohol has a fusion point below 60° C. and plays the role of a solvent. It is used excessively, at an alcohol/carboxylic acid ration of 1.5/1 to 3/1, or of 2/1. The alcohol and carboxylic acid mixture is heated in the presence of a catalyzer to a temperature ranging from 120 to 200° C., or from 140 to 160° C., under reduced pressure, between 200 and 800 mbar, until the acid is totally consumed. The catalyzer is a water-soluble acid, such as para toluene solufonic acid. The obtained compound of formula (I) is then purified through recrystallization.

The second synthesis route responds to the following reaction (when $R_1=R_2$):

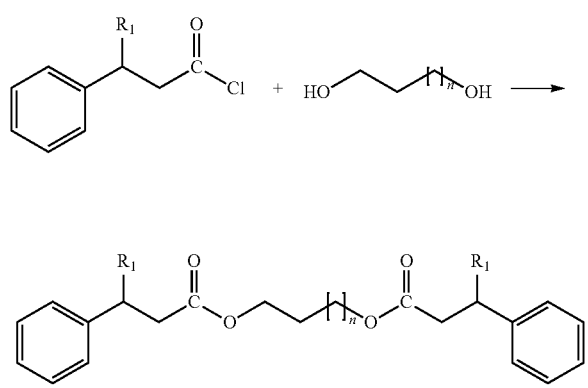

In this second synthesis route the alcohol is made soluble with a catalyzer in an aprotic polar solvent, such as tetrahydrofurane (THF). The catalyzer is a volatile base like triethylamine. The mixture is kept cold, at a temperature ranging from −20 to 20° C., or from 0 to 10° C. The mixture is kept cold in an ice bath or in a solid $CO_2$ bath immersed in a solvent such as acetone or ethanol. The mixture is advantageously kept inert by adding nitrogen. The acid chloride is then added slowly, preferably dropwise, over a period ranging from 15 to 60 minutes, preferably 30 minutes. The alcohol/acid chloride ration used is from 1.1/1 to 1/1.1, or 1/1. The temperature is then increased to room temperature (25° C.) and the mixture is kept at this temperature for 1 to 3 hours, preferably for 2 hours, under agitation. The compound of formula (I) obtained is then purified through recrystallization.

The compound of formula (I) is chosen from among the following compounds:

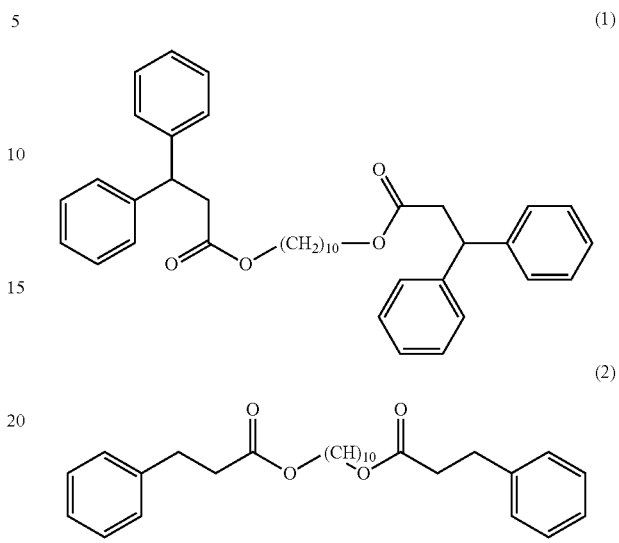

The fusion temperature of the compound of formula (I) may vary from 20 to 80° C., or from 30 to 80° C., or from 40 to 70° C. It is this optimal fusion temperature that makes the compound of formula (I) an ideal compound presenting the properties required to be used as a temperature change regulating agent in thermochromic pigment compositions.

In the thermochromic pigment composition, the ratios by weight of the compounds (A), (B) and (C) vary based on the nature and concentration of each of these compounds.

The ratio by weight of electron-donor organic dye compound (A) may vary from 1 to 10%, or from 1 to 6%, or from 2 to 4%, by weight in relation to the total weight of the thermochromic pigment composition.

The ratio by weight of electron-acceptor compound (B) may vary from 1 to 20%, or from 1 to 14%, or from 4 to 10%, by weight in relation to the total weight of the thermochromic pigment composition.

The ratio by weight of compound (C) of formula (I) playing the role of reaction medium may vary from 70 to 98%, or from 80 to 98%, or from 86 to 94%, by weight in relation to the total weight of the thermochromic pigment composition.

Thus, the thermochromic pigment composition may comprise:
(A) from 1 to 10%, or from 1 to 6%, or from 2 to 4%, by weight of at least one electron-donor organic dye compound,
(B) from 1 to 20%, or from 1 to 14%, or from 4 to 10%, by weight of at least one electron-acceptor compound, and
(C) from 70 to 98%, or from 80 to 98%, or from 86 to 94%, by weight of at least one compound responding to the formula (I).

According to an embodiment the thermochromic pigment composition comprises:
(A) from 2 to 4% by weight of at least one electron-donor organic dye compound,
(B) from 4 to 10% by weight of at least one electron-acceptor compound, and
(C) from 86 to 94% by weight of at least one compound responding to the formula (I).

The thermochromic pigment composition of the disclosure presents a color change hysteresis range ($\Delta H$) after encapsulation ranging from 20 to 80° C., or from 30 to 80° C., or from 40 to 70° C.

As an electron-donor organic dye compound (A), a non-limiting list may include classically known compounds such as diphenylmethane phthalides, phenylindolyl phthalides, indolylphthalides, diphenylmethane azaphthalides, phenylindolyl azaphthalides, fluorans, styrylquinolines and diazarhodamine lactones, examples of these compounds being presented below.

The electron-donor organic dye compound (A) can thus be chosen from among 3-(4-diethylamino-2-ethoxyphenyl)-3-(1-ethyl-2-methylindol-3-yl)-4-azaphthalide (Blue 63, CAS no.: 69898-40-4), 3,3-bis(p-dimethylaminophenyl)-6-dimethylaminophthalate (CAS no.: 1552-42-7), 2'-chloro-6'-(diethylamino)-3'-methylfluorane (CAS no.: 21121-62-0), 6'-(diethylamino)-1',3'-dimethylfluorane (CAS no.: 21934-68-9), 6'-(diethylamino)-1',3'-dimethylfluorane (CAS no.: 21934-68-9), 2-chloro-6-(dimethylamino)fluoran (CAS no.: 26567-23-7), 3-diethylaminobenzofluorane (CAS no.: 26628-47-7), 3',6'-bis(diethylamino)-2-(4-nitrophenyl)spiro[isoindole-1,9'-xanthene]-3-one (CAS no.: 29199-09-5), 2-phenylamino-3-methyl-6-diethylaminofluorane (CAS no.: 29512-49-0), 2'-(dibenzylamino)-6'-(diethylamino)fluorine (CAS no.: 34372-72-0), 2-(2,4-dimethylphenylamimo)-3-methyl-6-diethylaminofluorane (Black 15, CAS no.: 36431-22-8), 3-(1,2-dimethyl-3-indolyl)-3-[4-(diethylamino)-2-methylphenyl]phthalide (CAS no. 36499-49-7), 3',6'-dimethoxyfluorane (CAS no.: 36886-76-7), 3,3-bis-(1-butyl-2-methyl-indol-3-yl)-3H-isobenzofuran-1-one (Red 40, CAS no.: 50292-91-6), 3,3-bis-(2-methyl-1-octyl-1H-indol-3-yl)-3H-isobenzofuran-1-one (CAS no.: 50292-95-0), 2'-anilino-6'-[ethyl(p-tolyl)amino]-3'-methylspiro[isobenzofuran-1(3H),9'-[9H]xanthene]-3-one (CAS no.: 59129-79-2), 3-(4-diethylamino-2-ethoxyphenyl)-3-(1-ethyl-2-methylindol-3-yl)-4-azaphthalide (CAS no.: 69898-40-0), 3-(N-ethyl-n-isopentylamino)-6-methyl-7-anilino fluorine (CAS no.: 70516-41-5), 3-[4-(diethylamino)phenyl]-3-(1-ethyl-2-methyl-1H-indol-3-yl)phthalide (CAS no.: 75805-17-3), 2'-(2-chloroanilino)-6'-(dibutylamino)fluorine (CAS no.: 82137-81-3), 2-phenylamino-3-methyl-6-dibutylaminofluorane (CAS no.: 89331-94-2), 3-(1-butyl-2-methyl-1H-indol-3-yl)-6-(dimethylamino)-3-[4-(dimethylamino)phenyl]-3-1(3H)-isobenzofuranone (CAS no.: 92453-31-1), 7-(4-diethylamino-2-hexyloxyphenyl)-7-(1-ethyl-2-methyl-1H-indol-3-yl)-7H-furo[3,4-b]pyridin-5-one (Blue 203, CAS no.: 98660-18-5), 7,7-bis[4-(diethylamino)-2-ethoxyphenyl]furo[3,4-b]pyridin-5-one (CAS no.: 132467-74-4), N,N-dimethyl-4-[2-[2-(oxtyloxy)phenyl]-6-phenyl-4-pyridinyl]benzenamine (Yellow CK37, CAS no.: 144190-25-0), 3-(2,2-bis(1-ethyl-2-methylindol-3-yl)vinyl)-3-(4-diethylaminophenyl)-phthalide (CAS no.: 148716-90-9).

Preferably, the electron-donor organic dye compound (A) is chosen from among 3-(4-diethylamino-2-ethoxyphenyl)-3-(1-ethyl-2-methylindol-3-yl)-4-azaphthalide (Blue 63, CAS no.: 69898-40-4), 2'-(dibenzylamino)-6'-(diethylamino)fluorane (CAS no.: 34372-72-0), N,N-dimethyl-4-[2-[2-(oxtyloxy)phenyl]-6-phenyl-4-pyridinyl]benzenamine (Yellow CK37, CAS no.: 144190-25-0), 7-(4-diethylamino-2-hexyloxyphenyl)-7-(1-ethyl-2-methyl-1H-indol-3-yl)-7H-furo[3,4-b]pyridine-5-one (Blue 203, CAS no.: 98660-18-5), 2-(2,4-dimethylphenylamino)-3-methyl-6-diethylaminofluoran (Black 15, CAS no.: 36431-22-8) and 3,3,-bis-(1-butyl-2-methyl-indol-3-yl)-3H-isobenzofuran-1-one (Red 40, CAS no.: 50292-91-6).

As an electron-acceptor compound (B), a non-limiting list may include compounds having an active proton, such as compounds having a phenolic hydroxyl group (monophenols or polyphenols), their derivatives having substituents such as an alkyl group, an aryl group, an acyl group, an alcoxycarbonyl group, a carboxy group, esters of these, an amido group or a halogen atom, and condensed phenol-aldehyde resins such as bisphenols or trisphenols.

The following definitions are provided in the sense of the present disclosure:

Alkyl: a saturated aliphatic hydrocarbon group, linear or ramified, in $C_1$-$C_{20}$, $C_1$-$C_{12}$, $C_1$-$C_6$, or in $C_1$-$C_4$. The term "ramified" means that at least one lower alkyl group such as a methyl or an ethyl is carried by a linear alkyl chain. As an example of an alkyl group, the methyl, ethyl, n-propyl, 1-propyl, n-butyl, t-butyl and n-pentyl groups can be mentioned, for example.

Aryl: any functional or substituent group derived from at least one aromatic cycle; an aromatic cycle corresponds to any flat mono or polycyclic group comprising a delocalized π system in which each atom of the cycle comprises an orbital p, said orbitals p covering one another; among such aryl groups, the phenyl, biphenyl, naphthalene and anthracene groups can be mentioned. The aryl groups comprise 4 to 12 carbon atoms, or 5 to 6 carbon atoms. The aryl group may be, for example, a phenyl group.

Thus, the electron-acceptor compound (B) may be chosen from among the 2,2-bis(4-hydroxy-3-methylphenyl)propane (Bisphenol C, CAS no.: 79-97-0), 4-hexyl-1,3-dihydroxy-benzene (4-hexylresorcinol, CAS no.: 136-77-6), 4,4'-cyclohexylidenebisphenol (BZP, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-ethylidenebisphenol (CAS no.: 2081-08-5), 4,4'-(1,4-phenylenediisopropylidene)bisphenol (CAS no.: 2167-51-3), 1,1-bis(4-hydroxy-3-methylphenyl)cyclohexane (CAS no.: 2362-14-3), 9,9-bis(4-hydroxyphenyl)fluorine (CAS no.: 3236-71-3), 4,4'-(1,3-phenylenediisopropylidene) bisphenol (CAS no.: 13595-25-0), 1,1,1-tris(4-hydroxyphenyl)ethane (CAS no.: 27955-94-8), 4,4'-(2-ethylhexylidene) diphenol (CAS no.: 74462-02-5), α,α,α'-tris(4-hydroxyphenyl)-1-ethyl-4-isopropylbenzene (CAS no.: 110726-28-8), 4-(1,1,3,3-tetramethylbutyl)phenol (CAS no.: 140-66-9), 4-hydroxydiphenylether (CAS no.: 831-82-3), bis(2-hydroxy-1-naphthyl)methane (CAS no.: 1096-84-0), 4-(methylsulfonyl)phenol (CAS no.: 14763-60-1), 4-hydroxyphenyl-4'-isopropoxyphenyl sulfone (CAS no.: 95235-30-6), 4,4'-dihydroxybiphenyl (CAS no.: 92-88-6), 4-hydroxybiphenyl (CAS no.: 92-69-3), p-hydroxycumene (CAS no.: 99-89-8), 2,4-dihydroxybenzophenone (CAS no.: 131-56-6), hydroquinone monomethyl ether (MEHQ, CAS no.: 150-76-5), 3-n-pentadecylphenol (CAS no.: 501-24-6), 4-(2-phenylisopropyl)phenol (CAS no.: 599-64-4), 5-chloro-2-(2,4-dichlorophenoxy)phenol (CAS no.: 3380-34-5), N-(p-toluenesulfonyl)-N'-(3-(p-toluenesulfonyloxy)phenyl)urea (CAS no.: 232938-43-1), 2,2-bis(3,5-dibromo-4-hydroxyphenyl)propane (CAS no.: 79-94-7), 4,4'-isopropylidenediphenol (CAS no.: 80-05-7) and 4,4'-sulfonyldiphenol (BPS, CAS no.: 80-09-1).

Preferably, the electron-acceptor compound (B) is chosen from among 2,2-bis(4-hydroxy-3-methylphenyl)propane (Bisphenol C, CAS no.: 79-97-0), 4-hexyl-1,3-dihydroxy-benzene (4-hexylresorcinol, CAS no.: 136-77-6), 4,4'-cyclohexylidenebisphenol (BZP, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-(1,4-phenylenediisopropylidene)bisphenol (CAS no.: 2167-51-3), 1,1-bis(4-hydroxy-3-methylphenyl)cyclohexane (CAS no.: 2362-14-3), 9,9-bis(4-hydroxyphenyl) fluorine (CAS no.: 3236-71-3), 4,4'-(1,3-phenylenediisopropylidene)bisphenol (CAS no.: 13595-25-0), 1,1,1-tris(4-hydroxyphenyl)ethane (CAS no.: 27955-94-8), 4,4'-(2-ethylhexylidene)diphenol (CAS no.: 74462-02-5), and α,α,α'-tris(4-hydroxyphenyl)-1-ethyl-4-isopropylbenzene (CAS no.: 110726-28-8).

The thermochromic pigment composition is prepared by dissolving compounds (A) and (B) in compound (C) of formula (I), then agitating the same until a homogeneous mixture is obtained with the help of an agitator such as a homo mixer or a disperser.

Compounds (A) and (B) thus associated with compound of formula (I) can be formulated in the shape of microcapsules. Thus, the thermochromic pigment composition is encapsulated in microcapsules to form thermochromic pigment microcapsules. Such thermochromic pigment microcapsules constitute another technical objective according to the disclosure. They present advantageous characteristics in that they are resistant to mechanical constraints, insoluble and thus dispersible in water and present slow agglomeration.

The fusion temperature (or decoloration temperature T4) of the thermochromic pigment microcapsules may vary from 20 to 80° C., or from 30 to 80° C., or from 40 to 70° C.

The crystallization temperature (or recoloration temperature T1) of the thermochromic pigment microcapsules may vary from −40 to 20° C., or from −30 to 10° C., or from -20 to 0° C.

The thermochromic pigment microcapsules present an average diameter that may range from 0.5 to 30 μm, or from 1 to 10 μm, or from 3-5 μm. This average diameter corresponds to the D90 in volume and means that 90% by volume are made up of microcapsules having a size within the indicated interval. This average diameter can be determined by a granulometry laser using a Malvern Instruments Zetasizer Nano ZS.

The microencapsulation processes used include, but are not limited to, conventional methods such as:
chemical processes based on the in situ formation of the coating microcapsules, e.g. through polymerization or interfacial polycondensation, these processes being preferred,
physicochemical processes, e.g. phase separation or coacervation, solvent evaporation-extraction, thermally-induced gelation of emulsions (hot melt), or
mechanical processes, e.g. nebulization/drying (spray drying), gelation or congelation of drops, fluidized bed coating (spray-coating).

The thermochromic pigment microcapsules are advantageously made with an aminoplast resin base, or a melamine resin, urea resin or benzoguanamine resin base.

The thermochromic pigment microcapsules are prepared through in situ polymerization with a melamine resin.

Another technical objective relates to an ink composition comprising thermochromic pigment microcapsules according to the disclosure.

The thermochromic pigment microcapsules present within the ink composition represent from 5 to 50% by weight of the total weight of the ink composition.

The ink composition is furthermore primarily composed of water. Advantageously, water represents 40 to 80% by weight of the total weight of the ink composition.

The ink composition may likewise comprise one or more water-miscible co-solvents. Thus, the ink composition can contain an organic or aqueous solvent, or an aqueous solvent.

Among the solvents that may be added to the ink composition, are water and the polar water-miscible solvents, such as:
alcohols: linear or ramified alcohols in $C_1$-$C_{15}$, e.g. isopropanol, butanol, isobutanol, pentanol, benzyl alcohol; glycerine; diglycerine; polyglycerine
esters, e.g. ethyl acetate or propyl acetate,
carbonate esters, e.g. propylene carbonate or ethylene carbonate,
ketones, e.g. methyl isobutyl ketone (MIBK), acetone or cyclohexanone,
glycols, e.g. ethylene glycol, diethylene glycol, triethylene glycol, propylene glycol, polyethylene glycol, ethylene glycol monomethyl ether, 3-butylene glycol and thiodiethylene glycol,
amides, e.g. dimethylacetamide or dimethylformamide, and
mixtures thereof.

The solvent or solvents represent from 5 to 20% by weight of the total weight of the ink composition.

The ink composition may likewise contain one or more specific adjuvants that may play different roles according to the final intended application. These applications may relate to ink printing through serigraphy, offset printing, rotogravure printing, spray coating, electrostatic coating, electrodepositable coating, roll coating, inkjet printing and ink for writing tools such as ballpoint pens, fude pens, markers and colored pencils. The ink composition may also be added to a thermoplastic or thermosetting resin composition to form molds.

Among the adjuvants mentioned above, we can cite:
rheology modifiers (shear-thinning agents) capable of generating a gelling effect, e.g. xanthan gum or gum Arabic,
defoamers, e.g. modified aqueous dispersions of polysiloxane (MOUSSEX® from Synthron),
pH regulators, e.g. sodium hydroxide, triethanolamine,
surfactants, e.g. polyether polyols (TERGITOL™ from DOW),
biocides, e.g. isothiazolinones (ACTICIDE® from Thor),
corrosion inhibitors, e.g. benzotriazole,
lubricants,
dispersants,
coalescing agents,
crosslinking agents,
wetting agents,
plasticizers,
antioxidants,
UV stabilizers.

An additional technical objective relates to writing instruments comprising an ink composition according to the disclosure. These instruments are generally made up of a body comprising the ink composition, and possibly a friction element. The writing instrument according to the disclosure is advantageously chosen from among ballpoint pens, pencils, chalks, and even more advantageously ballpoint pens with friction-erasable ink. The friction element of the writing instrument is preferably an eraser.

The media on which the ink composition can be applied are paper, fibers, leather, plastic, glass, metal, wood and concrete.

In addition to the preceding provisions, the disclosure comprises further provisions that will result from the description complement to follow, which relates to the use of compounds of formula (I), to their characterization, and to their use as a temperature change regulating agent in thermochromic pigment compositions.

EXAMPLES

The compounds (1) and (2) of the following formulas:

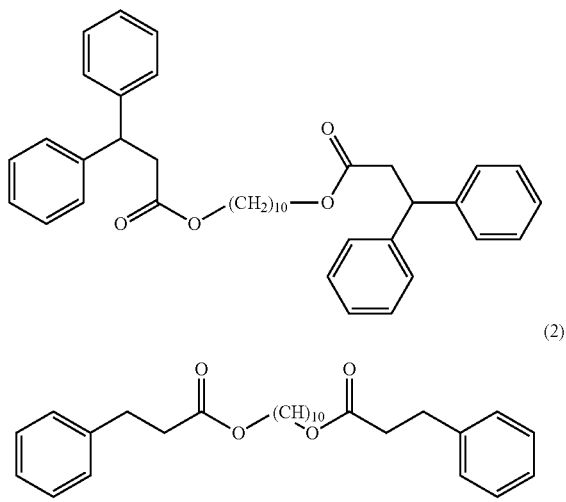

are prepared according to the following protocols:

Synthesis of Compound (1)

10 g of 1,10-decanediol (CAS no.: 112-47-0), 52 g of 3,3-diphenylpropionic acid (CAS no.: 606-83-7), and 200 mg of p-toluenesulfonic acid (PTSA) monohydrate (CAS no.: 6192-52-5) are mixed and headed to 140° C. for 6 hours, under reduced pressure (400 mbar).

The reaction medium is then made soluble in 150 ml of ethyl acetate. The organic phase is recovered and washed three times with 150 ml of water. The organic phase is then dried on sodium sulfate and the solvent is evaporated.

The product is recrystallized once using isopropanol and once using ethanol. The gaseous phase chromatography (GPC) analysis of the product obtained reveals that the product is pure at 95%.

Synthesis of Compound (2)

10 g of 1,10-decanediol (CAS no.: 112-47-0), 34.2 g of 3-phenylpropionic acid (CAS no.: 501-52-0), and 200 mg of p-toluenesulfonic acid (PTSA) monohydrate (CAS no.: 6192-52-5) are mixed and headed to 160° C. for 6 hours, under reduced pressure (400 mbar).

The reaction medium is then made soluble in 150 ml of ethyl acetate. The organic phase is recovered and washed three times with 150 ml of water. The organic phase is then dried on sodium sulfate and the solvent is evaporated.

The product is recrystallized once using isopropanol and once using ethanol. The gaseous phase chromatography (GPC) analysis of the product obtained reveals that the product is pure at 95%.

The fusion temperatures TFUS of the compounds (1) and (2) obtained are measured using differential scanning calorimetry (DSC) with a TA Instruments Q20 device, for a temperature range from −50 to 100° C., at cooling/heating speeds of +/−20° C./minute. The temperatures measured are indicated in Table 1 below.

TABLE 1

| Compound of formula (I) | $T_{FUS}$ (° C.) |
| --- | --- |
| Compound (1) | 71 |
| Compound (2) | 35 |

Preparation of a Thermochromic Pigment Composition

A thermochromic pigment composition is prepared by mixing 1.9 parts by weight of 3-(4-diethylamino-2-ethoxyphenyl)-3-(1-ethyl-2-methylindol-3-yl)-4-azaphthalide (compound (A), CAS no.: 69898-40-4), 2.1 parts by weight of 4,4'-(hexafluoroisopropylidene)diphenol (compound (B1) CAS no.: 1478-61-1), 2.1 parts by weight of 2,2-bis(4-hydroxy-3-methylphenyl)propane (compound (B2), CAS no.: 79-97-0) and 93.9 parts by weight of a compound of formula (I) according to the disclosure (compound (1)) (compound (C)):

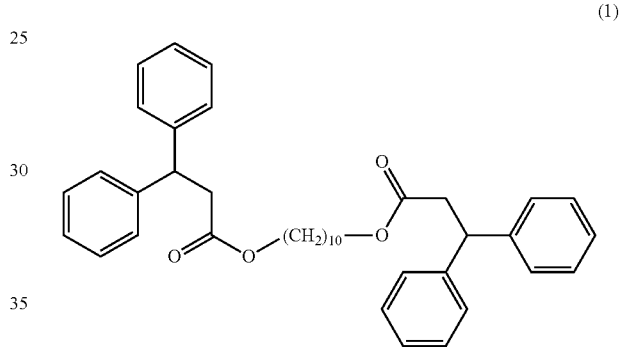

The mixture obtained is heated, under agitation, to a temperature of 110° C. for 45 minutes, until the compounds (A), (B1) and (B2) have been completely solubilized into the compound (C).

Preparation of Thermochromic Pigment Microencapsules 7.7 parts by weight of an aqueous solution of a copolymer of a maleic anhydride and methyl vinyl ether (33% solution by weight of the copolymer) are neutralized with 10.5 parts by weight of an aqueous solution of sodium hydroxide (1.0 M solution). This solution is diluted with 39.5 parts by weight of water, and the mixture emulsified with a homogenizer at a speed of at least 15 m·s$^{-1}$·25.3 parts by weight of the thermochromic pigment composition prepared before are added, and the emulsion obtained is kept at a temperature of 90° C. for 30 minutes. 17.0 parts by weight of a melamine-formaldehyde pre-polymer (50% aqueous solution by weight of the pre-polymer) are then added dropwise to the mixture. The reaction medium is then heated to a temperature of 90° C. and mixed at a speed of at least 15 m·s$^{-1}$ for 4 hours.

A slurry made up of thermochromic pigment microcapsules dispersed in an aqueous solvent is obtained, the microcapsules having a D90 diameter of 3.8 μm, determined using a Malvern Zetasizer Nano ZS system with an illumination of 632 nm.

The thermochromic pigment microcapsules obtained have the property of changing colors from blue to colorless beyond 71° C. with a color hysteresis effect.

Determination of the Decoloration and Recoloration Temperatures of the Thermochromic Pigment Microcapsules Prepared The transition temperatures of the thermochromic pigment microcapsules obtained are measured using differential scanning calorimetry (DSC) with a TA Instruments Q20 device, for a temperature range from −50 to 100° C., at cooling/heating speeds of +/−20° C./minute. The temperatures measured are indicated in Table 2 below.

TABLE 1

Transition temperatures of the thermochromic pigment microcapsules

| | Color change colored ↔ colorless | T1 (° C.) | T2 (° C.) | T3 (° C.) | T4 (° C.) | $T_H$ (° C.) | $T_G$ (° C.) | Δ H |
|---|---|---|---|---|---|---|---|---|
| Prepared thermochromic pigment microcapsules | blue ↔ colorless | −24 | −10 | 40 | 71 | −17 | 55 | 72 |

The transition temperatures measured are as follows:
T1: complete recoloration temperature,
T2: partial recoloration temperature,
T3: partial decoloration temperature,
T4: complete decoloration temperature, $$T_H = \frac{(T1 + T2)}{2}$$

$$T_G = \frac{(T3 + T4)}{2}$$

ΔH=hysteresis range=$T_G - T_H$

The invention claimed is:

1. A thermochromic pigment composition comprising:
(A) at least one electron-donor organic dye compound,
(B) at least one electron-acceptor compound, and
(C) at least one compound responding to the following formula (I):

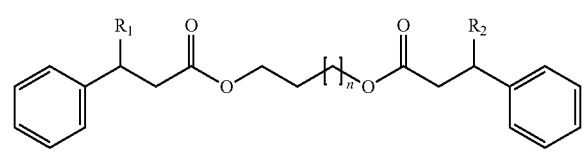

(I)

wherein:
  $R_1$ represents H or a phenyl group,
  $R_2$ represents H or a phenyl group, and
  n=1-8.

2. The thermochromic pigment composition according to claim 1, wherein the compound (C) responds to the following formula ($I_a$):

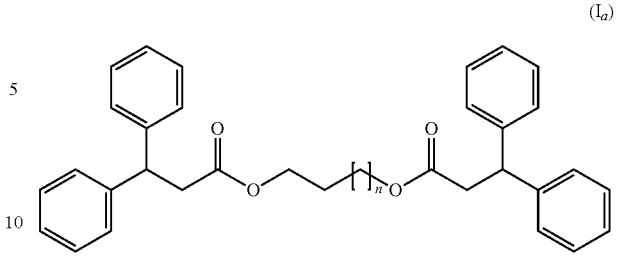

($I_a$)

wherein n=1-8.

3. The thermochromic pigment composition according to claim 1, wherein the compound (C) responds to the following formula ($I_b$):

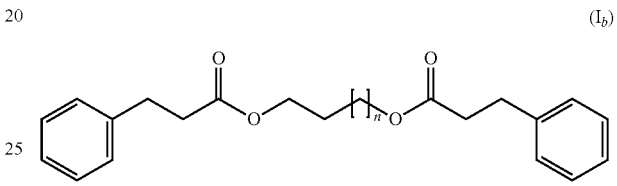

($I_b$)

wherein n=1-8.

4. The thermochromic pigment composition according to claim 1, wherein compound (A) is selected from the group consisting of 3-(4-diethylamino-2-ethoxyphenyl)-3-(1-ethyl-2-methylindol-3-yl)-4-azaphthalide (Blue 63, CAS no.: 69898-40-4), 2'-(dibenzylamino)-6'-(diethylamino) fluorane (CAS no.: 34372-72-0), N,N-dimethyl-4-[2-[2-(octyloxy) phenyl]-6-phenyl-4-pyridinyl]benzenamine (Yellow CK37, CAS no.: 144190-25-0), 7-(4-diethylamino-2-hexyloxyphenyl)-7-(1-ethyl-2-methyl-1H-indol-3-yl)-7H-furo[3,4-b]pyridine-5-one (Blue 203, CAS no.: 98660-18-5), 2-(2,4-dimethylphenylamino)-3-methyl-6-diethylaminofluoran (Black 15, CAS no.:36431-22-8) and 3,3,-bis-(1-butyl-2-methyl-indol-3-yl)-3H-isobenzofuran-1-one (Red 40, CAS no.:50292-91-6).

5. The thermochromic pigment composition according to claim 1, wherein the compound (B) is selected from the group consisting of 2,2-bis(4-hydroxy-3-methylphenyl)propane (Bisphenol C, CAS no.: 79-97-0), 4-hexyl-1,3-dihydroxybenzene (4-hexylresorcinol, CAS no.: 136-77-6), 4,4'-cyclohexylidenebisphenol (BPZ, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-(1,4-phenylenediisopropylidene) bisphenol (CAS no.: 2167-51-3), 1,1-bis(4-hydroxy-3-methylphenyl) cyclohexane (CAS no.: 2362-14-3), 9,9-bis(4-hydroxyphenyl)fluorine (CAS no.:3236-71-3), 4,4'-(1,3-phenylenediisopropylidene)bisphenol (CAS no.: 13595-25-0), 1,1,1-tris (4-hydroxyphenyl)ethane (CAS no.: 27955-94-8), 4,4'-(2-ethylhexylidene)diphenol (CAS no.: 74462-02-5), and α,α,α'-tris (4-hydroxyphenyl)-1-ethyl-4-isopropylbenzene (CAS no.: 110726-28-8).

6. A thermochromic pigment microcapsule comprising a composition according to claim 1.

7. An ink composition comprising thermochromic pigment microcapsules according to claim 6.

8. A writing instrument comprising an ink composition according to claim 7.

9. The writing instrument according to claim 8 chosen from among friction-erasable ink pens.

\* \* \* \* \*